United States Patent [19]

Kraska et al.

[11] 4,089,225
[45] May 16, 1978

[54] SYSTEM FOR RESIDUAL TIRE LIFE PREDICTION BY ULTRASOUND

[75] Inventors: Irvin R. Kraska, Lansing; Thomas A. Mathieson, Des Plaines; Richard N. Johnson, North Chicago; Wieslaw L. Lichodziejewski, Mt. Prospect, all of Ill.; David Leo Gamache, Sterling Heights; Leon Ash, Birmingham, both of Mich.

[73] Assignees: Gard, Inc., Niles, Ill.; The United States of America as represented by the Secretary of the Army, Washington, D.C.

[21] Appl. No.: 667,417

[22] Filed: Mar. 16, 1976

[51] Int. Cl.$^2$ .................................... G01N 29/04
[52] U.S. Cl. ......................................... 73/614; 73/627
[58] Field of Search ............... 73/67.8 R, 67.8 S, 67.9, 73/67.7, 67.6, 67.5 R, 67.2, 146

[56] References Cited

U.S. PATENT DOCUMENTS

| | | | |
|---|---|---|---|
| 3,336,794 | 8/1967 | Wysoczanski | 73/67.5 R |
| 3,640,122 | 2/1972 | Nusbickel | 73/67.9 |
| 3,673,860 | 7/1972 | Flaherty | 73/67.9 |
| 3,882,717 | 5/1975 | McCauley | 73/67.8 S |

OTHER PUBLICATIONS

Halsey, George H.; *Materials Evaluation*, "The Nondestructive Testing of Passenger Tires," pp. 137-142, Jul. 1968.

*Primary Examiner*—Richard C. Queisser
*Assistant Examiner*—Stephen A. Kreitman
*Attorney, Agent, or Firm*—Claron N. White

[57] ABSTRACT

A system, preferably a pulse echo reflection system, for residual tire life prediction by ultrasound includes: a transmitter transducer; means to provide pulses of electrical energy to the transmitter transducer, that converts the electrical pulses into pulses of ultrasonic vibrations and transmits them into an area of the plycontaining portion of the carcass of a tire, having a number of plies in the carcass, to be tested; clock means to control the frequency of the electrical pulses; a receiver transducer mounted relative to the transmitter transducer to receive ultrasonic energy reflected by the tire; amplifier means connected to the receiver transducer to receive reflected ultrasonic energy from different levels within that portion of the carcass of the tire, including reflected ultrasonic energy from plies of the carcass of the tire; processing means having an input connected to the amplifier; and gate means responsive to the clock means to provide, after a delay following each electrical pulse, a time-gated signal from the output of the amplifier means to the input of the processing means that, for each ultrasonic pulse to the tire, includes only the amplified signals corresponding to the reflected ultrasonic energy from a level adjacent but outwardly of the outermost ply of that portion of the carcass of the tire to a level inwardly of at least the outermost ply of that portion of the carcass. The processing means is constructed to provide a signal indicative of ply degradation or separation based on the time-gated signal.

14 Claims, 5 Drawing Figures

FIG. 2

CORD/RUBBER
CONDITION

A1  NORMAL  
A2

B1  LOOSE CORD  
B2

C1  CORD SEPARATION  
C2

*FIG. 5*

SYSTEM FOR RESIDUAL TIRE LIFE PREDICTION BY ULTRASOUND

GOVERNMENT CONTRACT

The invention herein described was made in the course of Contract DAAE07-73-C-0107 with the United States Department of the Army.

BACKGROUND OF THE INVENTION

1. Field of the Invention

There are many nondestructive inspection methods presently being applied to tires. These use X-radiography, infrared, holography and ultrasonic methods.

This invention relates to the testing of tires to determine their condition using nondestructive testing by a reflection pulse ultrasonic system.

2. Description of the Prior Art

Various pulse ultrasonic systems have been developed for inspection of tires. Known U.S. patents in this field are U.S. Pat. Nos. 2,378,237; 3,148,535 and 3,815,407.

U.S. Pat. No. 2,378,237 discloses a method and apparatus for ultrasonic testing of tires to locate separations or breaks in a tire carcass. In the system of that patent, ultrasonic waves are directed to strike a portion of a tire immersed in liquid. Resultant sound waves from another portion of the tire are picked up. This other portion is generally opposed to that portion of the tire receiving the sound waves. That other portion of the tire may be another peripheral portion or may be the inner portion in alignment with the outer surface to which the sound waves are applied. The picked up ultrasonic waves are changed by means to provide a sensuous indication using, for example, an oscillograph, a voltmeter, a rectifier and D.C. ammeter, or an oscillator. Relative movement between the tire and the ultrasonic waves imparted to the tire is effectuated to subject different portions of the tire to the ultrasonic energy. Any change in the sensuous indication that is noted during this relative movement indicates a separation or break in the tire because the change occurs as the ultrasonic waves are reflected or otherwise dispersed from a separation or break so that the ultrasonic wave is not transmitted to the indicator and thus is not registered by the indicator. The reflected ultrasonic energy is not received by the indicator. In use, the system of this patent provides an adjustment of the indicator so that there is a full scale deflection or trace of the indicator for a good portion of the tire being tested. An indicator is practically at a zero indication when during the relative movement between the tire and the transducer the portion of the tire containing a separation or break is under inspection. The system apparently provides this indication if the break is present at a portion or discrete portions about its periphery that can be compared with a portion that constitutes a good portion of the tire, that is, a portion that does not have a break or separation.

U.S. Pat. No. 3,148,535 discloses apparatus and a method for the inspection of tires using ultrasonic pulses to locate flaws and density changes caused by various foreign bodies, such as nails, in the tire, changes in the shape of the tire, etc. In the apparatus of that patent the ultrasonic transducer is used to impart ultrasonic energy to a wall portion of the tire and is used also to receive reflected ultrasonic energy from the wall portion of the tire so that the system is in this case a pulse-echo ultrasonic testing system. In a modification of the apparatus another transducer is mounted to scan in a radial direction for inspection of the rubber material on the periphery of the tire. The entire reflected ultrasonic energy is converted into electrical signals that are used to modulate a visual display means, such as a cathode ray tube, to present visible images or traces on the cathode ray tube.

The apparatus of this patent included means for rotating the tire by rotating the wheel on which the tire remains mounted. During this rotation the apparatus continuously scans a predetermined cross section of the tire using the pulse-echo ultrasonic testing system described above. Thereby a predetermined annular area of the tire is totally scanned during a complete rotation of the tire. The operation of the equipment, because of its construction, will provide a changing image pattern on the face of an image scope which pattern may be visually analyzed to determine the extent of the flaws or location of foreign bodies such as nails in the rubber of the tires.

Alternatively in the method of U.S. Pat. No. 3,148,535 a predetermined area of the wall of the tire also can be automatically scanned using the ultrasonic testing system with movement of the pulse-echo transducer and following the scanning of that area the wheel is turned so that a new area of the tire is in the scanning field. After each scanning of an area there is this intermittent turning of the wheel until the entire annular area of the wall of the tire has been scanned during one rotation of the wheel and tire. Apparently during these scans the transducer mounted for an inspection of the rubber material on the periphery of the tire is also operated to inspect the entire periphery, presumably of the width of tread, with an analysis of the trace from that scan to detect flaws and density changes. This alternative method, because of the construction of the equipment, also uses a changing image pattern that occurs around the tire if there are flaws or foreign bodies at one or more particular locations in the tire.

U.S. Pat. No. 3,815,407 discloses apparatus and method for tire inspection using ultrasonics. In the system the apparatus has a source transducer, i.e., a transmitter transducer, mounted to provide ultrasonic energy to the crown area of the tire, apparently at the center line of the tread, and has opposed receiver transducers mounted to receive ultrasonic energy from oppositely disposed points of the sidewalls of the tire being tested. The circuitry connected to the three transducers provides means to measure an imbalance in the transmission characteristics of the tire from the tread area to the oppositely disposed points of the sidewalls. The information collected permits identification of both the presence and nature of hidden defects. The tire is rotated during the testing procedure. Cuts, tread chunking, uneven wear, broken cords and ply separations will in general upset the symmetry of the tire. The defect detection of the invention of the patent is based on observing changes in symmetry and resonant frequency. The apparatus has means to control the frequency of the source transducer and during the rotation of the tire the frequency imparted by the source transducer to the tire is varied to compensate for changes in resonant frequency caused by physical variations in the tire. At the same time a lack of symmetry is detected in the transmission characteristics in the region of the casing by the pair of receiver transducers. The patent states that a ply separation will cause minimal change in resonant frequency but will change the damping and this change in damping with the defect off the plane of symmetry will unbalance the output of the two receiver transducers. When the separation or other defect in the tire is on the center line this will cause a change in the magnitude of the signals provided by both receiver transducers and because of the presence of the differential amplifier in the circuitry there is provided an indication of a symmetrical defect. The system of U.S. Pat. No. 3,815,407 is not a reflection ultrasonic system.

Australian investigators, using retreaded aircraft tires, have found that low-frequency, thru-transmission ultrasonic attenuation generally increases with tire age (i.e., number of times the tire is retreaded). The Australian airlines who use thru-transmission ultrasonic investigation to check retreading around the entire periphery of the tire have adopted a rule of rejecting any tire whose attenuation of signal is sufficiently great that defect observation is questionable. As a result, blown retreaded tires have been almost eliminated from the operation of the Australian airlines. This thru-transmission ultrasonic system for examining retreaded tires cannot discriminate between retread bond line anomalies and degraded plies of the carcass. Thus such system does not determine residual carcass life, unless the tire is buffed.

High-frequency ultrasonic instruments for nondestructive testing and thickness gauging of materials are commercially available. The test instrument utilizes transistorized circuits of printed circuit board construction and a cathode-ray tube (CRT) for video display of the test data. The instrument, that is capable of using either direct contact or immersion testing techniques and that can be used for single or dual transducer testing, includes: a power supply; a clock; a main bang generator; a sweep circuit; a receiver circuit; and a display circuit. The power upply provides the operating power to all the circuits in the tester. It also provides synchronization of triggering signals initiated by the clock. The clock triggering signals trigger the main bang generator and the sweep circuit simultaneously. When the main bang generator is triggered, it sends a pulse of electrical energy to the transducer and the receiver circuit. This pulse of electrical energy is called the main bang. The transducer converts the main bang into sound vibrations and transmits these sound vibrations into the object under test. The sweep circuit is triggered at the same instant the main bang generator is triggered. The sweep circuit provides the horizontal sweep voltage for the sweep trace which appears on the CRT. The horizontal sweep trace appears on the CRT shortly before the main bang because a built-in delay allows the sweep to start before the main bang. The received signals reflected by the boundaries from within the object under test are received by the transducer and applied to the receiver circuit. The receiver circuit amplifies and detects the received signals and converts these signals into video. The video signals from the receiver are applied to the display circuit and appear on the CRT. The display circuit permits the main bang, horizontal sweep and the received signals to be displayed on the CRT. The entire process is typically repeated 200 to 3000 times per second, depending upon the selected clock pulse frequency.

SUMMARY OF THE INVENTION

A tire during its life degrades due to age, use, and mileage interactions. The prime load-carrying structure, namely, the plies, loosen up (i.e., the cords in the plies become gradually more debonded from the surrounding rubber matrix). This degradation will reach a state where the plies become separated internally and with further use tread will separate from the tire at this degraded ply separation area, causing hazardous vehicle operation. Another cause of ply separation is a manufacturing induced effect. This is not degradation induced. Manufacturing separations are related to tire degradation, however, for most cases in a new, or slightly used, tight undegraded tire, manufactured-in separations will either not grow or grow in a slow controlled manner, but in a used, weakened, degraded carcass such separationswill grow quickly and thus potentially cause tire failure.

The system of the present invention predicts residual tire life (by sensing ply degradation) and finds both degradation-induced and manufactured-in separations by an ultrasonic inspection of the tire. The system is a reflection pulse ultrasonic system, preferably a pulse-echo type, rather than a pitch-catch type of reflection pulse ultrasonic system. The system is useful to examine portions of the carcass of the tire to provide information with respect to the condition of plies of the carcass. The processing means of the system in one of its simplest forms provides a signal, preferably as a digital readout, representing the condition of the outer plies of the carcass. That signal can be read and compared with the signal that the processing means would provide in the examination of a properly manufactured new tire.

The system of the invention, that is useful for the prediction of residual tire life by reflection ultrasound examination, includes: a transmitter transducer that converts high-frequency electrical pulses into pulses of ultrasonic vibrations and transmits them into an area of the ply-containing portion of the carcass of a tire, having a number of plies in the carcass, to be tested; clock means to provide signals at its output; means to provide pulses of high-frequency electrical energy at its output connected to said transmitter transducer, said pulse-providing means having an input connected to said output of said clock means that by its pulses initiates and controls the frequency at which the high-frequency electrical pulses are provided by said pulse-providing means to said transmitter transducer; a receiver transducer mounted relative to said transmitter transducer to receive ultrasonic energy reflected by the tire; amplifier means including an amplifier having an output and an input connected to said receiver transducer to receive reflected ultrasonic energy from different levels within that portion of the carcass, including reflected ultrasonic energy from plies of the carcass of the tire; gate means having a gate with an output and an input connected to said output of said amplifier, said gate means being constructed to be responsive to the operation of said clock means to provide, after a delay following each electrical pulse, a time-gated amplified signal at the output of said gate that, for each ultrasonic pulse to the tire, includes only the amplified signals corresponding to the reflected ultrasonic energy from a level adjacent but outwardly of the outermost ply of that portion of the carcass of the tire to a level inwardly of at least the outermost ply of that portion of the carcass; and processing means having an input connected to said output of said gate and constructed to sense the nature of the time-gated amplified signals and to provide a signal, in visual readout form, that is an indication of the condition of the plies of the carcass of the tire.

The system of the invention can be used in a number of ways. The system can be used to inspect the tire while it is rotating or it can be used to inspect different areas, as sampled areas, while the tire is stationary. The inspection can be at the sidewall area, at the shoulder area, or at the tread area of the tire, either for degradation or for separations.

The construction of the processing means to sense the nature of the amplified signals based on the conversion of the reflected ultrasonic energy from the tire is dependent upon the particular embodiment of the system. The processing means in the preferred embodiment is constructed to sense the time-gated amplified signals for the presence of peaks of amplitude that vary from the amplitude of time-gated amplified signals that are obtained when the system is used to examine a properly manufactured unused tire. In that case the system has its processing means constructed to provide a reject signal in the event that the amplitude of any time-gated amplified signal obtained during an inspection of a tire actually is greater than the amplitude of time-gated amplified signals obtained by a conversion of the reflected ultrasonic signals from plies of a properly manufactured new tire (this indicates separation presence). Lower signal indicates degradation presence. In this case, the sampled inspection of a stationary tire will provide by the processing means a separation reject signal when it senses that any peak of the time-gated amplified signals exceeds a predetermined value. In this embodiment, that senses for peaks in signals, the system when used for inspection of a rotating tire is modified to include summing means to sum the peak signals from different areas of the tire to provide a digital readout that indicates, when it is below a predetermined digital value, that the tire is no longer in a condition for further use.

In the event that the system is constructed for its use to inspect a rotating tire, in which the inspection is entirely around the tire, the summing means of the processing means can operate during this one revolution of the tire to total all of the time-gated amplified signals. In that construction of the sytem, the processing means includes an analog-to-digital converter means to provide a conversion of the summed signal to a digital signal. That digital signal is supplied to a digital display panel and has a value dependent upon the condition of the plies of the carcass. In this case the summed signal is different than that obtained by a sampled inspection of a stationary tire. However, the value of the summed signal is still dependent upon the condition of the plies of the carcass providing the reflected ultrasonic energy. Furthermore, that digital value can be compared with the digital value obtained by an inspection with rotation of a properly manufactured new tire. This embodiment requires a coordination with the speed of rotation of the tire under inspection to ensure that each area of the tire is weighted similarly during the period of summing of the time-gated signals.

In the other embodiments of the invention, the processing means converts the time-gated amplified signals from the amplifier means to a readable form indicative of the nature of the amplified signals. This construction of the processing means can be one of a number of different types that can include an integration of the time-gated amplified signals.

Some organizations, including governmental agencies, have a large number of vehicles stationed at one site and for a maximum use of the tires for these vehicles necessitates an extensive retreading program. Thus a simple, low-cost, reliable system of determining the integrity of a tire carcass prior to the retreading operation is very desirable to avoid a considerable expense that would occur if faulty tires are retreaded. Conventionally the tires are selected for retreading on the basis of a visual inspection and classification technique that culls out all tires with visible defects. It is believed that no low-cost method is available to detect internal defects that cannot be seen at the surface of the tire.

Those tires that pass this visual inspection are sent to a retreading facility where they are buffed, i.e., subjected to a grinding procedure to remove the old tread. During this buffing operation, the operator sometimes can detect separations by sound and he will then reject the tires that he detects as containing separations. Some governmental agencies at least require the return of the rejected tires and this provides a further undesirable transportation cost along with the cost of buffing a tire that is rejected as a result of the operator detecting separations during the buffing operation.

The system of the present invention permits the examination of tires at the site at which the vehicles are located to determine whether those tires, not culled out by visual inspection, have sufficient integrity of the tire carcass to warrant retreading. The system of the present invention also permits periodic inspection of tires having adequate tread and free of visual defects that would warrant ceasing further use. This periodic use of the system for examination of a tire during the life of the tread permits a decision to cease use of the tire, before retreading becomes apparent, because the carcass has lost its integrity to the extent that the further use would be inadvisable if not dangerous. In this periodic inspection by the system of the invention tires that have not lost sufficient integrity of the carcass to require cessation of use can be programmed for a shorter period of further mileage use, than the mileage between periodic inspections, before further examination of the carcass for integrity.

As mentioned earlier, the system of the present invention is a reflection system. To maximize resolution and sensitivity, the system operates at the highest practical frequency of each electrical pulse provided to the transmitter transducer. The system provides a depth discrimination capability to examine the condition of the plies of the carcass independent of the presence of any retread bond line signal. Thus the gate means operates to open its gate after the time that it would receive such retread bond line signal from the amplifier means and the gate is kept open for a period of time to receive the amplified signals that indicate the condition of the plies of the carcass.

In the reflection pulse ultrasonic inspection system of the present invention, the gate means, when suitably adjusted for degradation reading on a particular type of tire, examines only that part of reflected ultrasonic energy that is from the carcass plies. Thus the reflected energy, that is gated to the processing means after amplification, does not include reflected ultrasonic energy from defects occurring in the tread of the tire.

In the event that there is a weak tread bond, the reflection from this level of the tire thickness will reduce the ultrasonic energy to the plies and thereby reduce the reflected energy from the plies but not enough to provide any problem in the use of the system. Furthermore, localized defect effects are negated, in one embodiment, by signal summation around the entire tire, and in the other embodiment by an examination of two or more areas to determine an "average" signal indicative of the condition of the plies. If the weak tread bond is general, that is, extends along the entire circumference of the bond line around a particular tire being examined and a more accurate degradation reading is desired, the tire could be buffed and the carcass examined in accordance with this embodiment of the system of the present invention to obtain reflected ultrasonic energy data indicative of the condition of the plies and the resultant electrical signals can be used to provide a comparison with a carcass having the same ply construction but without degradation of the plies.

If the degradation of the carcass during service has proceeded only to the point that there is a loosening of the cords of the various plies and not to separation, then the reflected ultrasonic pattern from the various plies will be approximately the same but the reflected energy will be less than that from the plies of the tire before its service use. In this case, the system using a circumferential inspection sums the output of amplifier means receiving electrical signals produced by the receiver transducer by the conversion only of the reflected ultrasonic energy from the various plies. In this case also, the summed signal in the system of the invention is compared with a reference signal. If the summed signal for the tire after service use is below a predetermined percentage of a reference signal, the tire is considered to be no longer available for service use. If the summed signal for that tire is greater than this predetermined percentage of the reference signal and no previous inspection provided a substantially lower summed signal, this information can be used, based on experience, to decide a reasonable amount of continued service use permissible before another inspection. This permits continued service use until a subsequent inspection indicates the carcass so sufficiently degraded that the tire would fail.

the reference signal mentioned above is based on a signal corresponding to that obtained by summing signals obtained from the receiver transducer based on reflected ultrasonic energy only from the plies of the carcass of a tire of proper manufacture and having no service use. Of course, the signals from the transducers are amplified before summing.

Similarly, in the non-rotating tire mode of this invention amplitude comparisons are used to determine the degradation level in the tire, with a lower signal indicating more tire degradation.

The above systems describes a simple degradation-separation system (i.e., signals higher than a new tire reference indicate separation; lower indicate degradation). This approach dictates a very quick transition (in the tire life process) from a degraded to a degradation-induced separated tire. For practical purposes, this happens to be a valid assessment (i.e., few transitional separated tires are found). More sophisticated signal processing, in which the separation signal amplitude is between that of a low degradation and a tight, new tire, can be used to identify transitional tires.

Such a processing system illustratively includes gate means that provides a dual gating of the amplified electrical signals and further includes second processing means. In this case the gate means provides some of the amplified signals to one of the processing means and the rest of the amplified signals to the other processing means. The modified system has comparator means that compares the outputs of the two processors to determine whether the two processed amplified signals are in the proper ratio to constitute an indication of carcass degradation or separation presence. If the comparator means shows a substantial difference resulting from the required comparison of the two signals, this indicates substantial degradation with separation of the outermost plies. If such degradation is present, the tire should be rejected as not suitable for further service use.

DESCRIPTION OF THE DRAWINGS

FIG. 1 also shows one embodiment of one of the preferred alternative processor, namely, a system containing peak sensing means and level sensing means, that provides a voltage to a reject light means that has a light that is lit when the amplitude of the signal to the level sensing means exceeds a predetermined value indicating the tire has separation and should be rejected.

FIG. 2 shows also an alternative aspect of this preferred embodiment.

DETAILED DESCRIPTION

In the drawings the same component is generally given the same number, except when a component is a second component of a type already assigned a number.

The embodiments of the pulse-echo ultrasonic inspection system of the present invention, are shown in FIGS. 1 through 4. In all embodiments the system includes a pulse-echo transducer 11 that functions as a transmitter transducer and a receiver transducer. It is shown placed against the crown of the tire generally indicated at 12. The tire 12 is shown as a fragmentary view taken at the midline, i.e., the plane of symmetry of the tire with transducer 11 contacting the tread at this midline. In the schematic view of tire 12 it is indicated that tire 12 includes a carcass 13 containing layers of plies and bonded to the outer surface of carcass 13 is the retread 14 that is contacted by transducer 11. The tire 12 has its ply layers in carcass 13, the retread bond line and the tire tread surface shown in FIG. 1 by legends, while the third legend appears only in FIGS. 2, 3 and 4.

Figure 1:
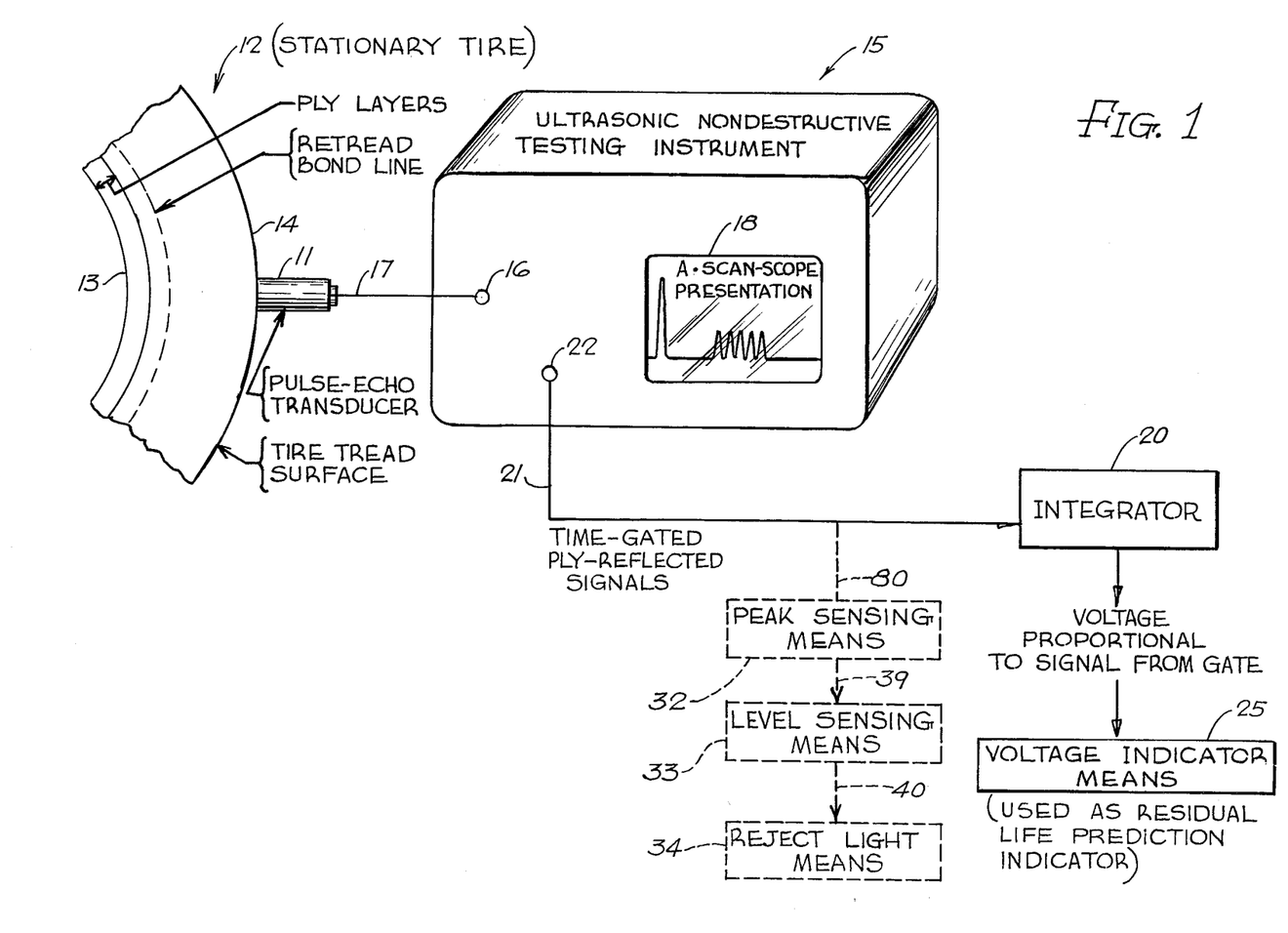
FIG. 1 is a schematic drawing of one embodiment of the system of the invention, for testing a stationary tire, that uses a pulse-echo transducer and uses a conventional ultrasonic tester having an output providing amplified signals, based on the output of the transducer, to a processor (in this case an integrator) that provides a voltage to the indicator means.

The system in the aspect shown in FIG. 1 includes an ultrasonic nondestructive test instrument, illustratively, Sonic Model FTS Mark I, generally indicated at 15. This instrument has a connector 16, at one of its panels, that is connected by a line 17 to transducer 11. The instrument 15 provides the pulses of high-frequency electrical energy to connector 16 and thereby to transducer 11 that provides pulses of ultrasonic energy to tread 14 of tire 12 and thereby to carcass 13. The plies in carcass 13 reflect ultrasonic energy back through tread 14 to transducer 11 before the next high-frequency electrical pulse is provided by instrument 15 to transducer 11. The reflected ultrasonic energy is received by transducer 11 that converts it to electrical signals that are sent to instrument 15 through connector 16. These electrical signals are amplified by instrument 15 that provides from the amplified signals an A-scan that is displayed by its CRT 18. This presentation on CRT 18 is illustrated schematically on FIG. 1 to show a pip resulting from the first reflection, that is from the interface between transducer 11 and the outer surface of tread 14, and the subsequent pips resulting from reflections from the outermost ply to the innermost ply of carcass 13. The gate means of instrument 15 can be adjusted to a time-gating period such that the visual display does not include a pip based on the main bang signal from the main bang generator and the pip based on the reflected ultrasonic energy from the interface between transducer 11 and the outer surface of tread 14. After these adjustments the visual display on CRT 18 constitutes the display of amplified electrical signals corresponding to the reflected energy signals from within the tread and the carcass. The time-gating that provides this adjustment can be further adjusted to visually display on CRT 18 the amplified electrical signals, as an A-scan, based on reflected energy from only the carcass and a small innermost portion of the tread to include the bond line, and preferably adjusted to display as pips only the amplified electrical signals based on the reflected ultrasonic energy only from the carcass.

The embodiment of the system shown in FIG. 1 includes integrator means 20 that has the input of its integrator connected by a line 21 to a connector 22. The connector 22 is connected to the output of the amplifier of instrument 15 through the adjustable gate means of instrument 15. That gate means is adjusted to provide to integrator 20 the amplified electrical signals corresponding to reflected energy signals from the carcass alone or the carcass plus a small inner portion of the tread.

The integrator means 20 has the output of its integrator connected to voltage indicator means 25. This output from integrator means 20 is the voltage proportional to the signal provided at connector 22 of instrument 15 while the gate of the gate means of instrument 15 for the time-gating is open; thus with the adjustment of the gate means, as described above, this voltage is proportional to the reflected ultrasonic energy from the plies of carcass 13 and, if the adjustment includes in the time-gated period any reflected ultrasonic energy from the retread bond line, this voltage is proportional to the combination of the reflected ultrasonic energy from that bond line and the plies of carcass 13.

The voltage indicator 25, in the aspect of the embodiment of the system shown in FIG. 1, provides a numerical value that can be read, and recorded if desired, by an operator of little skill and training. That numerical indication can be compared with a predetermined minimum value to determine whether the tire should have further service use. The reference numerical value will not be the same for all tires because tires have different use factors (i.e., loads, pressures, mileages, road, off-road, airplane applications) which affect the rate of degradation in particular tires in given applications.

Information comparable to that received by voltage indicator means 25 will be displayed on CRT 18 as a number of pips, not in the form of an integrated voltage representing the combined amplitudes of the pips. It would require an experienced operator to correlate the visual display on CRT 18 with a reference display representation that would indicate the predetermined minimum height of the pips that would justify continued use of the tire being tested and to determine, if the tire is not rejected, the amount of service use permitted before the next inspection. Numerical records for simplified record-keeping to be used with a subsequent inspection for comparison with preceding inspection for analysis would be feasible in applications where the cost is justifiable.

The use of instrument 15 to amplify the electrical signals from transducer 11 and to gate the signals before or after amplification to provide suitable signals for a time-gated period to integrator 20 with adjustment of the time-gating of instrument 15 has the advantage when instrument 15 is adjusted so that during the time that the gate is open any electrical signal based on a reflected ultrasonic energy from the bond line will be seen on CRT 18. Furthermore, there is the advantage that, if there is a sufficient degradation of the outer ply to constitute a cord separation and the bond line between the tread and the carcass is not weak, the display on CRT 18 will indicate by the height of the first pip, representing the reflected ultrasonic energy from the outermost ply that the tire has already had its carcass degraded to the extent of cord separation of this outermost ply and thus the tire should be rejected as unsuitable for further service use. Although there is this advantage, the display on CRT 18 when there is no cord separation but just loose cords an experienced operator is required to make a decision and furthermore the cost of the instrument justifies the modification shown in FIG. 4 that merely uses some of the components of test instrument 15 as a separate, less expensive package.

Figure 2:
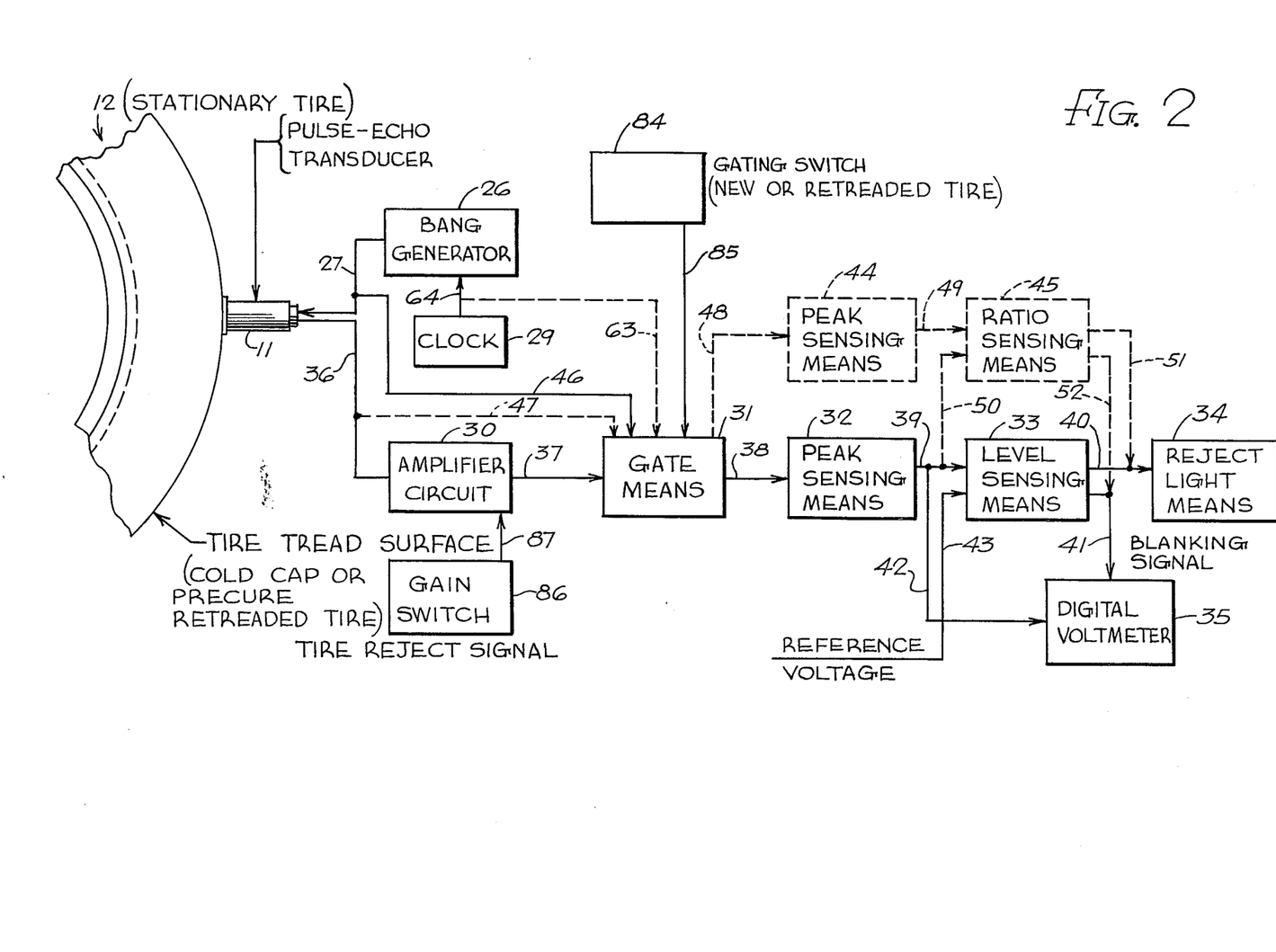
FIG. 2 is a block diagram showing the preferred embodiment of the system for testing a stationary tire. The system contains only those components of the conventional ultrasonic tester of FIG. 1 that are used in the system of the present invention along with the peak sensing means, the level sensing means and the reject light means.

Referring to FIG. 2, one aspect of that preferred embodiment of the system of the invention includes pulse-echo transducer 11 and a bang generator 26 that provides pulses of high-frequency electrical energy by a line 27 to transducer 11. The bang generator 26 is triggered, in its operation, to provide each pulse by clock means 29.

This preferred embodiment of the system for inspection of a stationary tire further includes an amplifier circuit 30, gate means 31, peak sensing means 32, level sensing means 33, reject light means 34 and a digital voltmeter 35. The input of the amplifier of amplifier circuit 30 is connected by a line 36 to pulse-echo transducer 11. A line 37 connects the output of amplifier circuit 30 to the input of a gate of gate means 31. A line 38 connects the input of peak sensing means 32 to the output of the gate of gate means 31. A line 39 connects the output of peak sensing means 32 to an input of level sensing means 33. A line 40 connects one output of level sensing means 33 to the input of reject light means 34. The other output of level sensing means 33 is connected by a line 41 to an input of digital voltmeter 35. The other input of digital volmeter 35 is connected by a line 42 to line 39.

The level sensing means 33 is constructed to provide a voltage signal at its output connected by line 40 to reject light means 34 whenever the amplitude of the signal at its input from peak sensing means 32 exceeds a predetermined amplitude. When this voltage is applied to that output of level sensing means 33, the other output of level sensing means 33 provides a voltage, as a blanking signal, by line 41 to digital voltmeter 35.

The digital voltmeter is constructed to convert the amplitude of the signal, to its input from peak sensing means 32 by lines 39 and 42, to a digital display but the operation of digital voltmeter 35 does not display the digital value when digital voltmeter 35 is provided with a voltage signal from level sensing means 33 by line 41.

The level sensing means 33 has another input that is connected by a line 43 that is provided a reference voltage by a voltage source (not shown). The level sensing means 33 includes an operational amplifier and lines 39 and 43 are connected to two inputs of the operational amplifier that provides at its output a voltage when the voltage in line 39 exceeds the voltage provided by line 43. The level sensing means 33 is illustratively constructed further with two transistors that are conducting when there is this voltage output of the operational amplifier. The base of each of these transistors is connected to the output of the operational amplifier. The emitter of each transistor is connected to ground.

One of the transistors has its collector connected by a coil of a relay to a voltage source. The switch of the relay is normally open but it is closed when the transistor is conducting. The line 40 is connected to one contact of the switch and to the light of reject light means 34 that is connected to one line of an AC power source (not shown). The line connected to the other contact of the switch of the relay is connected to the other line of the AC power source. Thus, when that transistor is conducting, the switch closes and current flows through the light that is then lit to signal the operator that the tire should be rejected.

The collector of the other transistor is connected to line 41 so that the signal is provided in line 41 when this transistor is conducting.

The gate means 31 includes circuitry that is initiated by a pulse to provide, after a delay, the opening of the gate of gate means 31 and to maintain the gate open for a period of time that is the time-gated period mentioned above. To initiate this circuitry gate means 31 has its circuitry connected by a line 46 to line 27 so that the pulse provided by bang generator 26 initiates the operation of the circuitry of gate means 31 to open the gate of gate means 31 after the delay mentioned above.

In the schematic drawing of FIG. 2, line 36 is shown as connected to transducer 11 and not to line 27 connecting bang generator 26 to transducer 11. Since lines 27 and 36 are both connected to transducer 11, the high-frequency electrical pulse on line 27 would be transmitted to line 36 if line 36 is connected directly to the same connector of transducer 11. When lines 27 and 36 are connected to the same connector or line 36 is connected to line 27, and it is desired to eliminate the transfer of the pulse in line 27 to amplifier circuit 30 by line 36, the amplifier circuit 30 can include switch means (not shown) that connects the input of the amplifier of amplifier circuit 30 by line 36 to transducer 11, after each pulse in line 27, for a predetermined period of time. This switch means can be responsive to the trailing edge of a pulse in line 27. Alternatively, each pulse from clock means 29 can control the initiation of this operation of the switch means to pass a signal from transducer 11 to amplifier 30 for a predetermined period of time.

FIG. 2 shows in dotted lines additional components that are present in the alternative aspect of the preferred embodiment of the system for testing a stationary tire. These additional components are a peak sensing means 44 and ratio sensing means 45. In this alternative aspect, level sensing means 33 is not present and thus line 43 is absent. Also, gate means 31 is constructed with two gates, each with an output. In this construction of gate means 31 one of the gates is the gate described above that is triggered by the pulse in line 27 connecting bang generator 26 to transducer 11, because that gate is connected by line 46 to line 27. Thus, after the predetermined delay that gate opens for the predetermined time-gated period mentioned above. The other gate is connected by a line 47 to line 36 so that the second gate is triggered by the first echo signal of each pulse to open that gate after a predetermined delay for a predetermined period of time. In this construction the second gate opens, after its delay, following the opening of the first gate. Thus the output of the second gate does not include for each echo pulse the first one or few of the amplified voltage signals from transducer 11 but rather only later amplified voltage signals resulting from reflections of inner plies, whereas the amplified voltage signals passing through the first gate further includes the amplified voltage signals resulting from the reflections of the outermost ply or plies.

The output from the second gate of gate means 31 is connected by a line 48 to the input of peak sensing means 44. The output of peak sensing means 44, representing the maximum voltage input to it after the ultrasonic pulse, is connected by a line 49 to one input of ratio sensing means 45 while the other input of ratio sensing means 45 is connected by a line 50 to line 39 and thus to the output of peak sensing means 32.

One output of ratio sensing means 45 is connected by a line 51 to line 40 that is connected to the output of reject light means 34. The other output of ratio sensing means 45 is connected via a line 52 and line 41 to the blanking input of digital voltmeter 35 while the other input of digital voltmeter 35 is connected, as in the other aspect of the embodiment, via lines 42 and 39, to the output of peak sensing means 32.

The ratio sensing means 45 includes an operational amplifier and circuitry connected to the two inputs of the operational amplifier and to lines 49 and 50. The circuitry is constructed so that the output of the operational amplifier provides a voltage signal when the ratio of the voltages in lines 50 and 49 exceeds a predetermined ratio. This output of the operational amplifier is connected to the base of the two transistors mentioned above in the other aspect of this embodiment. One of the transistors has its collector connected by lines 51 and 40 to reject light means 34 while the collector of the other transistor is connected by lines 52 and 41 to the blanking input of digital voltmeter 35. As a result, the voltage signal from the operational amplifier of ratio sensing means 45 is provided, when the ratio mentioned above exceeds the predetermined ratio, to reject light means 35 to turn on its light and the voltage signal, that is provided to lines 52 and 41, blanks the operation of digital voltmeter 35. When this ratio is not exceeded, digital voltmeter 35 is operative so that the voltage applied via line 42 to the input of digital voltmeter 35 is converted and displayed as a digital value representing that voltage.

Figure 3:
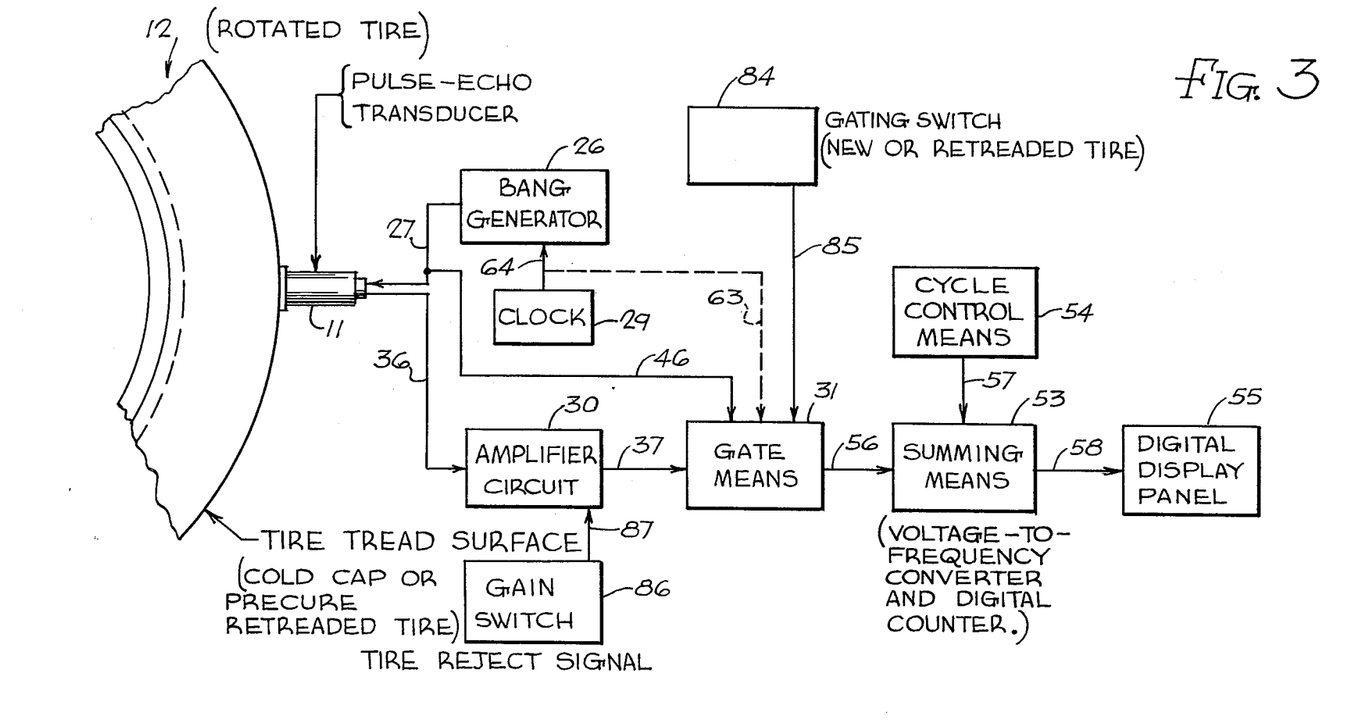
FIG. 3 is a block diagram showing the preferred embodiment of the system for testing a tire during one complete rotation of a tire. As in the embodiment of FIG. 2, the system of claim 3 contains only those components of the conventional ultrasonic tester of FIG. 1 that are used in the system of the present invention. In the embodiment of FIG. 3, those components are used along with summing means, a digital display panel and cycle control means that controls the operation of the summing means so that it operates only during each test of a tire, namely, during one complete revolution of the tire.

Referring to FIG. 3, that preferred embodiment of the system of the invention is used in the inspection of a rotating tire. In that use, the system is operated from the time of the start of the rotation of a tire and ceases operation when the tire has been rotated 360°. As in the preferred embodiment of FIG. 2, the embodiment of FIG. 3 includes pulse-echo transducer 11, bang generator 26, amplifier circuit 30, gate means 31 and clock means 29. The gate means 31 has only one gate as in the first aspect of the preferred embodiment in FIG. 2. Instead of peak sensing means 32, etc., used as components in the system of FIG. 2, the system of FIG. 3 includes summing means 53, cycle control means 54 and digital display panel 55. The output of gate means 31 is connected by a line 56 to the input of summing means 53. The output of cycle control means 54 is connected by a line 57 to another input of summing means 53. The output of summing means 53 is connected by a line 58 to an input of digital display panel 55.

The cycle control means 54 controls the initiation of the motor (not shown) that rotates tire 12 for one complete revolution. At the time it initiates this operation of this motor it initiates the operation of summing means 53 by providing an output signal to line 57 that initiates the operation of summing means 53. At the completion of the single revolution of tire 12, cycle control means 54 stops the operation of the motor rotating tire 12 and no longer provides the signal by line 57 to summing means 53. During this operation of summing means 53, ultrasonic pulses are provided to tire 12 and the echoes from each of these pulses are provided to amplifier circuit 30. The amplified signals are provided to gate means 31 that had the one gate mentioned earlier opened, after a delay, for a time-gated period following each pulse from bang generator 26. During each time-gated period summing means 53 receives the amplified voltage signals from amplifier circuit 30. The summing means 53 includes a voltage-to-frequency converter and a digital counter to convert, for each ultrasonic pulse, the amplified voltage output of amplifier circuit 30 to a digital value and to sum these digital values in the digital counter. The outputs of the digital counter are connected by lines, identified herein by line 58, to input signals to digital display panel 55 that provides a digital numerical display representing the summed amplified voltages resulting from the pulse echoes during the period of time that tire 12 is rotated.

Figure 4:
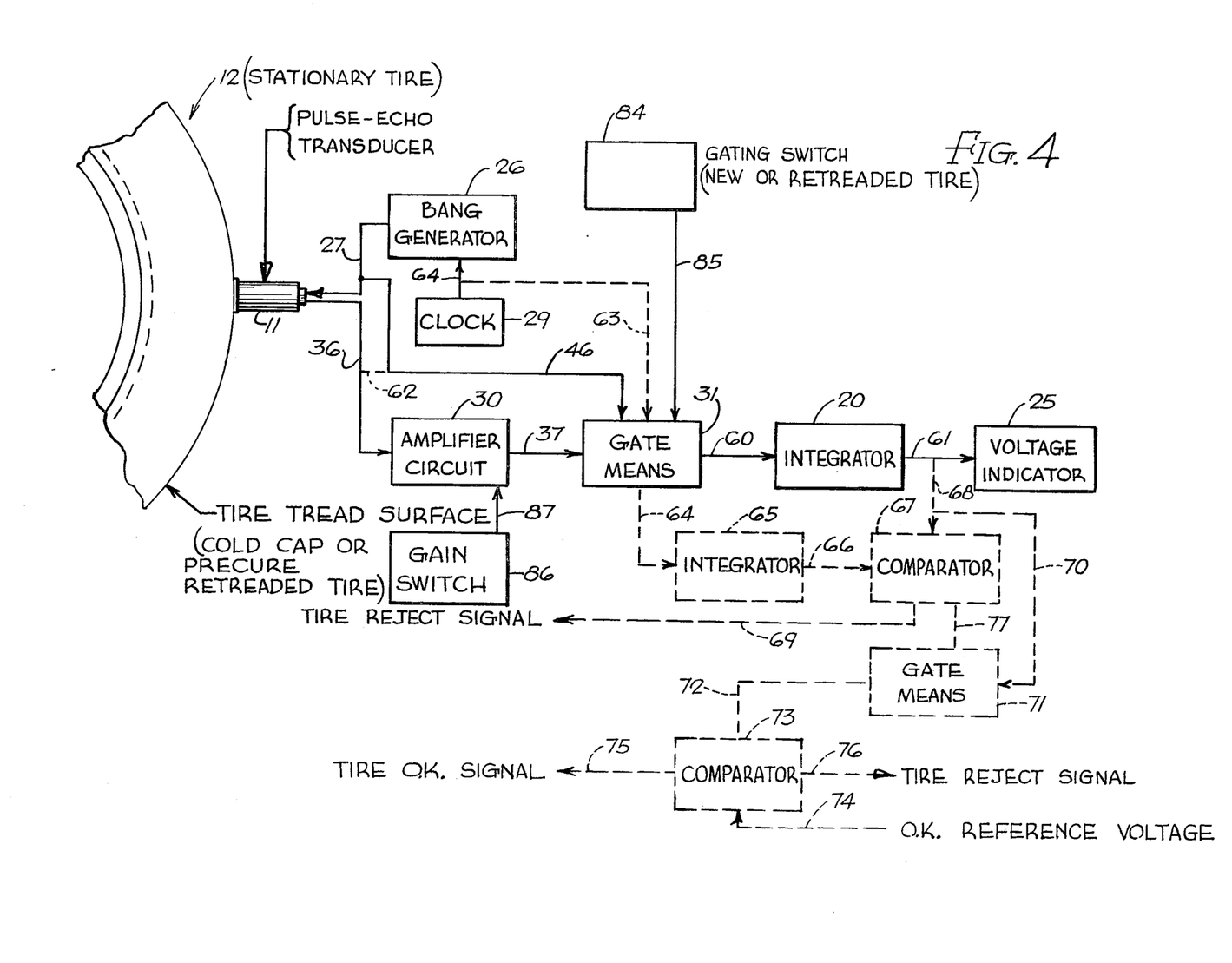
FIG. 4 is a block diagram showing another embodiment of the system for testing a stationary tire. The system contains only those components of the conventional ultrasonic tester of FIG. 1 that are used in the system of the present invention along with integrator means and voltage indicator means responsive to the voltage output of the integrator and shows in dotted lines alternative aspects of this embodiment of the system.

Referring to FIG. 4, this embodiment of the system in the invention for inspection of a stationary tire includes pulse-echo transducer 11, bang generator 26, amplifier circuit 30, gate means 31 and clock means 29. The gate means 31, except for the additional capabilities described later, has only one gate as in the first aspect of the preferred embodiment in FIG. 2. The system of FIG. 4 includes integrator means 20 and voltage indicator means 25 as in the case of the embodiment shown in FIG. 1.

The gate means 31 of FIG. 4 includes the circuitry that is initiated by a pulse to provide, after a delay, the opening of the gate of gate means 31 and to maintain the gate open for a period of time that is the time-gated period mentioned with respect to the first aspect of the embodiment in FIG. 2. To initiate the circuitry, gate means 31 has its circuitry connected by line 44 to line 27 so that the pulse provided by bang generator 26 initiates the operation of the circuitry of gate means 31 to open the gate of gate means 31, after the delay mentioned above. The line 36 connecting amplifier circuit 30 to transducer 11 is connected directly to the latter rather than via line 27 or is connected by line 27, as described earlier in connection with FIG. 2. The output of gate means 31 is connected to the input of the integrator of integrator means 20 by a line 60. The output of the integrator is connected by line 61 to the input of voltage indicator means 25 that can be an analog voltmeter or, preferably, digital voltmeter 35 (FIG. 2).

In FIG. 4 gate means 31 connects the output of the amplifier of amplifier circuit 30 to the input of the integrator of integrator means 20. The initiation of the operation of gate means 31 is by a pulse in line 46 provided by a pulse from bang generator 26, as described above. Instead of gate means 31 being connected to line 27 by line 46, gate means 31 can be connected to line 36, as shown for a modified construction, by a line 62 connected to line 46, that in this case is not connected to line 27 so that the circuitry of gate means 31 is initiated in its operation for the predetermined time-gated period, after a delay, if desired, by a first pulse in line 36. That pulse can be the pulse in line 27 or, if there is the switch described above, to prevent this pulse reaching amplifier circuit 30, the initiation is provided, after each ultrasonic pulse to tire 12, by the signal based on the first reflected ultrasonic energy from the tire, namely, from the interface of tire 12 and the transducer 11. In a further modification, the circuitry of gate means 31 can be connected instead by a line 63 to a line 64 connecting the output of clock means 29 to the input of bang generator 26 so that the gate is opened for a predetermined time-gated period after a predetermined delay initiated by each pulse in line 64. A further modification (not shown) of the embodiment of FIG. 4 is the location of gate means 31 between transducer 11 and amplifier circuit means 30 instead of between the latter and integrator means 20.

FIG. 4 shows in dotted lines additional components that are present in the system for additional capabilities when the voltage of the output voltage signal on line 61 is a value that is at least equal to the predetermined minimum value for a tire to be acceptable for continued service use with or without retreading but not at least a predetermined maximum value indicating ply separation. In that modification gate means 31 is constructed with two gates, each with an output, and with means, such as described above for the alternative aspect of the preferred embodiment of FIG. 2, so that, by operation of switch means, as a part of the circuitry, for a first time-gated period one gate is open to transmit from amplifier circuit 30 amplified signals to line 60 and during the second time-gated period, when the first gate closes, the other gate is open to transmit amplified signals by a line 64 to an input of an integrator of integrator means 65. In this modification the first gate has a shorter time period than the normal time-gated period, without the operation of the switch means. The output of the integrator of integrator means 65 is connected by a line 66 to comparator means 67.

The gate means 31 can be constructed to provide, from amplifier circuit means 30, two time-gated signals initiated after delays and triggered for the first time-gated period by a pulse of bang generator 26 and triggered for the second time-gated period by the signal in line 36 resulting from the first echo pulse, for each pulse in line 27 to transducer 11, can be provided by circuitry in gate means 31 connected to line 61 so that the circuitry is responsive to a predetermined minimum voltage level in line 61. Other gating combinations can be used which will provide multi-channel information in the spirit of this invention.

This operation of the circuitry, as logic control, occurs after a pulse in line 27, when the voltage signal in line 61 is greater by a predetermined minimum value and less than a predetermined maximum value that would be either basis for the rejection of the tire. The output voltage signal from integrator means 65, that is passed to comparator means 67 by line 66, is compared with the voltage output signal from integrator means 20 that is connected to another input of comparator means 67 by a line 68 connected to line 61. In this modification, integrator means 20 includes a sample-and-hold circuit, to hold the voltage output of the integrator of integrator means 20 for the period of time that there is no input signal to integrator means 20 but rather an input signal to integrator means 65, so that the integrity of the output signal of integrator means 20 is maintained to compare with the output signal of integrator means 65 by comparator means 67. The control logic can enable comparator means 67 at the end of the second time-gated period, i.e., at the completion of the transfer of the signal to integrator means 65.

In the event that the ratio of the voltage inputs by lines 68 and 66 to comparator means 67 is greater than a predetermined value, comparator means 67 provides, at an output connected to a line 69, a tire reject signal. This is because that ratio indicates that at least the first outermost ply has degraded beyond cord loosening to a cord separation. This cord separation was the reason that the preceding pulse in line 27 provided reflected ultrasonic signals for conversion to electrical signals that, after amplification and integration by integrator means 20, provided the voltage signal in line 61 that is greater than a predetermined minimum voltage. If there is no tire rejection signal on line 69 and if voltage indicator means 25 shows that the voltage signal from integrator means 20 had exceeded a predetermined minimum voltage the operator can consider the tire satisfactory for further use after retreading.

If the tread has sufficient depth to justify further service use without retreading and the voltage on line 61 is indicated by voltage indicator means 25 to be relatively close to the minimum voltage, the operator can determine, based on tire service experience, and can specify the maximum amount of service use, i.e., mileage, of the tire before reinspection.

Instead of a determination by an operator reading voltage indicator means 25, another modification of the system, as shown in FIG. 4, includes a line 70 connected to line 68 and to an input of a gate of gate means 71. The output of that gate is connected by a line 72 to a comparator means 73 that has another input connected by a line 74 to an O.K. reference voltage provided by a voltage source (not shown). The control logic, mentioned above, can, in this case, be responsive to the voltage of the signal in line 61 if the voltage is greater than the predetermined minimum value required for the tire suitable for further service use or retreading. When this voltage signal in line 61 is thus sufficiently low to operate the logic control means, the control logic can enable the gate of gate means 71 to provide the integrated voltage signal from line 61 to line 72 and thereby to comparator means 73. At the same time the logic means enables the operation of comparator means 73 that provides an output signal, that is a tire O.K. signal, to a line 75 when the ratio of voltages in lines 74 and 72 does not exceed a predetermined value, or provides an output signal, constituting a tire reject signal, to a line 76 if this ratio exceeds that predetermined value.

Instead of the logic control means directly controlling gate means 71, comparator means 67 can have an output connected by a line 77 to an input of gate means 71 to enable it whenever comparator means 67 is not enabled so that the signal in line 61, after a pulse in line 27, has, for the normal time-gated period that the first gate is open, i.e., the period providing the examination of the entire depth of the carcass, the integrated voltage signal representing all reflected ultrasonic signals from plies of the carcass 13. Of course, the operation of comparator means 73 is still controlled by the logic control means. While comparator means 67 is operating there is no signal in line 77 to enable gate means 71.

The foregoing description of FIG. 4 shows the versatility of this embodiment of the sytem of the invention by adding additional components, as described above, to provide for automatic operation to eliminate decision-making by an operator.

From the foregoing description of modifications of the system of FIG. 4, it is apparent that comparator means 67 and comparator means 73 constitute two other voltage indicator means to determine the suitability of the tire for further use and/or retreading.

FIG. 1 also shows one of the preferred embodiments of the system in which the processing means is constructed to sense for peaks of amplitudes of time-gated signals. In this modification, the processing means is peak sensing means 32 that has its input connected by a line 80 to line 21. In this modification integrator 20 and voltage indicator means 25 are absent.

The peak sensing means 32 provides a voltage signal by line 39 to level sensing means 33 that is connected by line 40 to reject light means 34 as described in FIG. 2. The light is lit when peak sensing means 32 is provided a signal with an amplitude greater than the amplitude of the signals resulting from the reflected ultrasonic energy from plies of a properly manufactured new tire. Other types of processing rather than integration or peak sensing can be used within the spirit of this invention.

New tires by virtue of their manufacture do not normally have a bond line between the tread and the carcass. Such bond line always occurs in a retreaded tire. Accordingly, if it is desired to avoid the slight probability of a separated retread bond, the time-gating of the amplified signals to provide the proper time for initiation of the transfer of amplified signals, for each ultrasonic pulse, from the amplifier means to the processing means can be initiated to open the gate, i.e., the first gate if there are two gates in the alternative constructions, at an earlier time for the new tire than is the case for a retreaded tire that is initiated at a later time to avoid any signal from the retread bond line. Accordingly, the system of the invention can include a gating switch 84 that has two positions. In this event, circuitry of gate means 31 is constructed with an alternative means to provide a different time delay. Each of the two means to provide a time delay is, when operative, responsive to the signal from clock 29 to initiate, after the delay, the operation of the gate means. When the switch is in one position, for the new tire, the time delay is shorter than when the switch is in the other position that is used when the tire to be inspected is a retreaded tire. This gating switch 84 is shown schematically to be connected by a line 85 to gate means 31 but, of course, the switch is a part of the construction of gate means 31 in this modification.

There are two processes for retreading tires after suitable buffing. One is sometimes called a "precure" process and the other is called a "hot cap" process. The density of the rubber of the tread of the retreaded tire used in the "precure" process may differ from the density of the rubber of the tread of the retreaded tire of the "hot cap" process. Because of this, the system is modified to take this fact into consideration in the amplification of the electrical signal resulting from the conversion by the transducer of the reflected ultrasonic energy. For this purpose the embodiments of the system shown in FIGS. 2, 3 and 4 are modified to show that amplifier circuit 30 includes means to provide two different gains of amplifier circuit 30. The gain chosen is determined by the retreading process used to make the retreaded tire to be inspected. The amplifier circuit 30 has a gain switch 86 schematically indicated to be connected by a line 87 to amplifier circuit 30 but actually switch 86 is a part of amplifier circuit 30. In one position gain switch 86 provides the desired gain for amplifier circuit 30 for one of these two types of retreaded tires and the switch in the other position provides the other gain desired for use of the system in the inspection of the other type of retreaded tire. This two-gain position control has been found adequate for commercial tire use, so far. Military vs. commercial tread also requires a gain change.

Because tires to be tested can have substantially different tread thickness the amplifier circuit 30 can include means to automatically increase the gain of the amplifier during the period of time that it is receiving from transducer 11 voltage signals resulting from each ultrasonic pulse provided by the voltage pulse from bang generator 26. This increase in gain is initiated by the first voltage signal received from transducer 11 due to the reflection of ultrasonic pulse by the interface between transducer 11 and tread 14 of tire 12. This is a distance-amplitude circuitry that compensates that tread thickness in the use of the inspection of the invention.

The pulse-echo ultrasonic tire inspection system of present invention resulted from our discovery after an extensive evaluation of 500 used military vehicle tires, and particularly of a documented 500 tire test of a series of tire sizes (with number of each size inspected shown in parenthesis) included. 7:00 × 16(45); 7:50 × 15(25); 9:00 × 16(200); 9:00 × 20(153); and 11:00 × 20(77). These tires were retread candidate tires and they were ultrasonically inspected in five critical areas (midline, shoulders and sidewalls). Each of the tires was evaluated to establish retread bond line condition, internal casing defects, and "background noise."

The equipment used for the pulse-echo ultrasonic testing of the tires comprised the commercial instrument Sonic Model FTS Mark I, a tire rotating fixture and a water tank to provide continuous coupling of high-frequency ultrasonic energy into the tire. The tire-handling equipment was a modified Branick Tire Spreader, a pneumatic lift table, and a rotary bearing to allow tire angular motion. The operating procedure was as follows: the tire was rolled onto the air-operated lift to allow the casing to be raised slightly above the inner bead hooks; the hooks each moved laterally outward to engage the inner bead of the casing; each of the six inside arms of the spreader, controlled by the main air cylinder, moved outward to engage the outer bead casing and to spread the tire to any desired width; and a spreader with the tire mounted on it was lifted above the walls of the water tank, rotated 90° and lowered into the water tank. After ultrasonic inspection of the tire the operating procedure was reversed to remove the tire. The Sonic Model FTS Mark I was modified to incorporate a 1200 V. pulser and an 0.1–2 MHz broadband receiver. The pulser was operated at 3000 pulses per second.

Thirty-six tires which presented ultrasonic defect indications were sectioned, visually examined, and/or mechaniclly tested to determine the nature and location of the source of the ultrasonic indications. From the data obtained by these tests it was concluded that there are two classifications of defects: localized and circumferential. Localized defects are defined as those with ultrasonic indications which were observed at discrete positions around the circumference of a tire (i.e., small ply separations, inclusions, porosity, etc.); circumferential defects are defined as those with ultrasonic indications which persisted throughout most, or all, of a single continuous 360° rotation of the tire during the inspection.

Comparison of ultrasonic test results with visual examinations and physical test data confirmed that 5% of the tires had localized defects and 42% had circumferential defects. Further correlations of ultrasonic test results with visual and mechanical test data led to a concept of the pulse ultrasonic system of the invention to provide a measure of carcass degradation and thus the potential remaining useful tire life or to determine whether a tire is retreadable or nonretreadable.

The results obtained from this study showed that there can be detection of localized and circumferential defects by means of pulse-echo ultrasonic inspection. Defect incidence led us to the conclusion that the detection of circumferential defects rather than detection of localized defects will provide a better measure of tire carcass integrity (i.e., retreadability).

One-fifth of the localized defects observed consisted of miscellaneous type defects (inclusions, porosity, cord packing density, and breaks). Four-fifths of the localized defects consisted of separation type defects (cord, ply or ply overlap edge separations). Sixteen tires, that presented localized ultrasonic defect indications, were sectioned and examined. Visual confirmation was obtained for each of the ultrasonic indications. In the remaining areas of the sectioned tires, where no defect indications were observed, visual inspection showed no localized defect was present. Of the 16 tires that were sectioned and examined, 12 of the localized defects that were observed by the ultrasonic tester consisted of ply separations, cord separations and ply overlap edge separations. The localized defects in the other four tires could be attributed to the inclusion of foreign material within the plies, porosity or reduced cord packing density.

As mentioned above, 42% of the tires inspected had circumferential defect indications. Of these 210 tires, 91 tires had circumferential defects that were found to be associated with a weak tread bond, 54 tires had circumferential defects that were only cord separations or outer ply deterioration and 64 tires had circumferential defects that were only loose cords. Twenty tires exhibiting circumferential defects by the ultrasonic inspection were sectioned, visually examined and subjected to a peel test. All ultrasonic indications were confirmed.

Of those tires that showed a weak tread bond by providing a high tread bond line signal, none was found in the two smallest size tires. The percentage of the other three tires of increasing size were 53 out of 200 tires, 32 out of 153 tires, and six out of 77 tires. Of the A-scan displays for the tires showing circumferential defects, a number of these also had a high tread bond line signal. Sketches B1 and C1 of FIG. 3 depict A-scan recordings of tires that do not have the weak tread bond but have the indication of loose cord and cord separation, respectively. In sketches B1 and C1, as well as in sketch A1, there is a pip at the far left that indicates at least the end portion of the reflected signal from the tread outside surface.

The A-scan visual patterns of the tires permitted recognition by the operator of the presence of the high tread bond line reflection in tires also showing a condition with loose cord or cord separation. By this operator observation, it was determined that there was 16 tires of the 80 tires exhibiting loose cord defects that also had the high tread bond line signal so that 64 of the tires of the 500 tires had only the loose cord defect such as shown in sketch B1. It was also determined that six of the tires exhibiting cord separation also had the high tread bond line signal so that 54 of the 500 tires had only a cord separation defect such as shown in sketch C1. Thus a large number of tires that had defects in the ply did not have the weak bond of the tread to the carcass.

Figure 5:
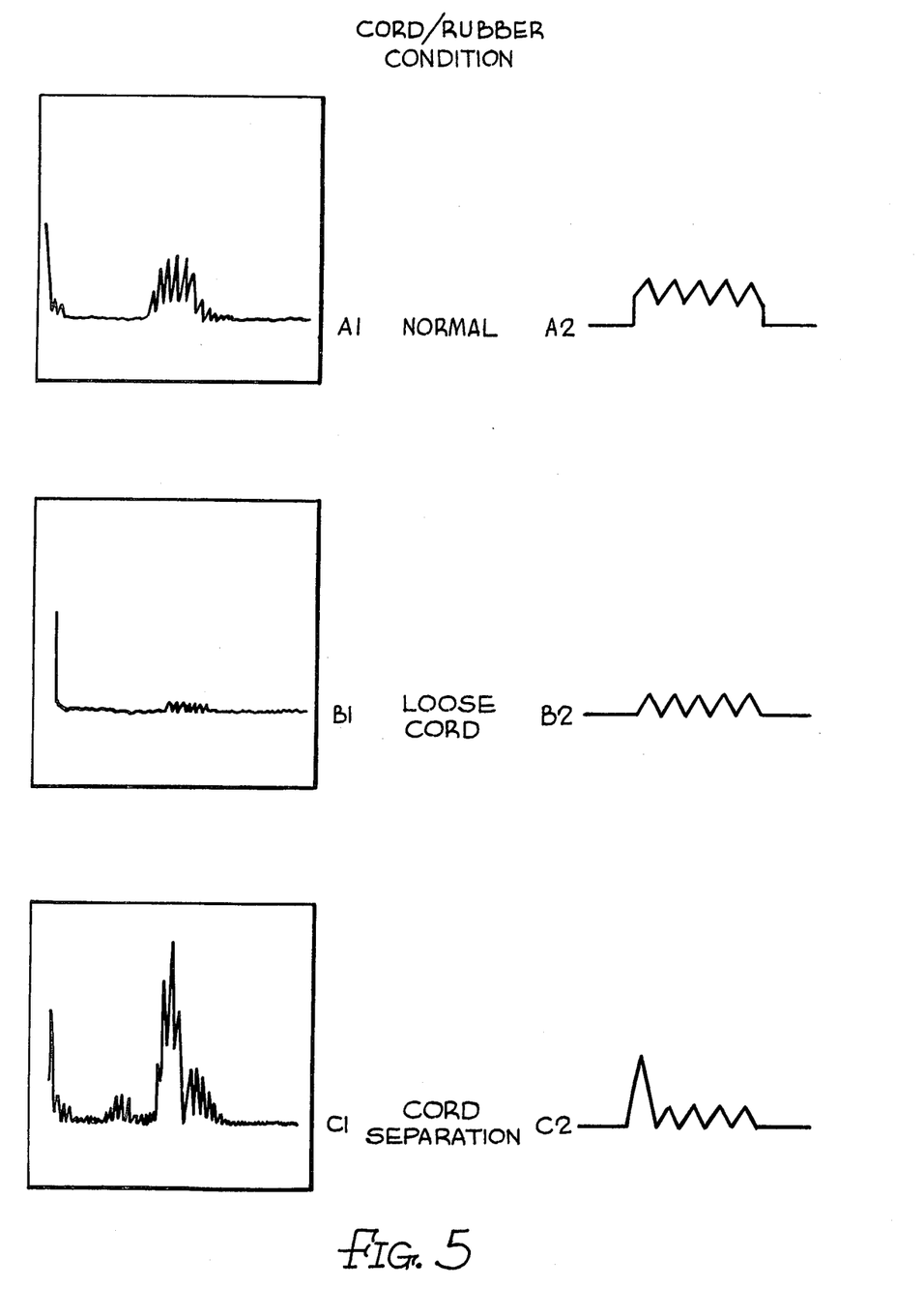
FIG. 5 shows in A1, B1 and C1 representative A-scans of ultrasonic CRT traces of the midline of typical tires representing, respectively, the normal scan obtained with a satisfactory tire having no service use, with a tire having an amount of service use that resulted in a loosening of the cords of the plies of the tire, and with a tire having an amount of service use that resulted in further degradation of the carcass so that there is a cord separation of the outermost ply of the carcass of the tire. A2, B2 and C2 represent idealized traces of the tires having their traces depicted in A1, B1 and C1, respectively.

Tests of the intraply average peel strength versus the ultrasonic classification of reflection of normal, low and high, represented by sketches A1, B1 and C1 and idealized by sketches A2, B2 and C2, respectively, in FIG. 5, were 42 ± 12 lb./in., 38 ± 5 lb./in. and 27 ± 3 lb./in. based two tires/five samples each, three tires/five samples each, and three tires/five samples each respectively. Significance was measured using the T-test of Sample Means. This yields P, a measure of the probability of the difference between the mean strength of tires of different reflection numbers is not due to chance. The P for the average peel strength for the tested tires having the low ultrasonic reflection was greater than 40% and P for the average peel strength having high ultrasonic reflection was greater than 99%.

In the testing described above, it is mentioned that the test instrument was used to provide 1200 V. This high voltage was used to be sure to obtain adequate reflection from the plies of the carcass of a tire especially from the 12-ply rated tire that is used in large vehicles, such as large military vehicles. The bang generator of the system of the present invention, to provide from the carcass adequate reflection signals that are amplified and integrated, provides a voltage greater than 500 V. and preferably greater than 1000 V. Also, the receiver band width is illustratively a width between 0.1 and 2.0 MHz. Other voltages and band widths might be desirable to optimize inspections for other applications.

In view of the fact that the system is constructed to detect reflected ultrasonic signals from the carcass and a small depth of the inner portion of the tread adjacent the bond line, and preferably only from the carcass, and because the reflections evaluated are from circumferential defects or essentially so, the system does not require a relative movement between the tire and the transducer, e.g., rotation of the tire, to determine degradation of the tire. Instead, the system of the present invention provides a suitable inspection of the tire on a wheel while the wheel is on the vehicle. It is not necessary to raise the vehicle for an examination with a rotation of the wheel. Instead, the operator places the transducer against the tread of the tire at a few spaced areas at the midline or at an area of the midline and laterally on the tread between the midline and the shoulders for only a few examinations. The system can provide a detection in most cases by placing the transducer at the midline at one area that is a small part of the periphery of the tire.

In the specification the term "carcass" has been used. The carcass of a tire is the tire structure except tread and sidewall rubber. The term "casing" is used by some persons to refer to the carcass of a tire.

The system of the invention is useful in inspection of the various types of tires, namely, bias ply tires, belted ply bias tires, and belted radial tires. The system can process the time-gated signals generated from the reflected ultrasonic signals from the plies in the carcass that are below the tread, that are in the shoulders, or that are in the sidewalls.

The foregoing description has been presented solely for the purpose of illustration and not by way of limitation of the invention because the latter is limited only by the claims that follow.

We claim:

1. A pulse ultrasonic reflection system, useful for residual tire life prediction by monitoring cord/rubber condition of at least one ply of a tire carcass, which comprises:

a transmitter transducer that converts high-frequency electrical pulses provided to its input into pulses of ultrasonic vibrations for transmittal into an area of the multi-ply containing portion of the carcass of a tire to be tested;

clock means to provide voltage signals at its output;

means having an input and an output, said means being constructed to provide a pulse of high-frequency electrical energy at its output after it is triggered by each voltage signal that is received at its said input, said pulse-providing means having an input connected to said output of said clock means that by its periodic voltage signals initiates and controls the frequency at which the high-frequency electrical pulses are provided by said pulse-providing means to said transmitter transducer;

a receiver transducer, that in the system is either mounted relative to said transmitter transducer to provide a pitch-catch type or is constructed with said transmitter transducer to provide a pulse-echo type of pulse ultrasonic reflection system, to receive ultrasonic energy reflected by the tire after each ultrasonic pulse provided to the tire by said transmitter transducer, said receiver transducer having an output that provides voltage signals based on said received reflected ultrasonic energy;

amplifier means including an amplifier having an output and an input that is connected to said output of said receiver transducer;

gate means having first and second inputs and having a gate with an output, said gate means having: its said first input connected to said output of said amplifier; and its said second input connected to one of said outputs of said receiver transducer, said pulse-providing means and said clock means, said gate means being constructed to be responsive to a voltage signal at said second input of said gate means to open said gate of said gate means, after a predetermined delay, for a predetermined period of time to provide time-gated voltage signals at said output of said gate, after each pulse is provided by said pulse-providing means to said transducer, based on the reflected ultrasonic energy only from the interior portion of the tire, that includes at least one ply of the tire, to which the ultrasonic energy is applied by said transmitter transducer;

processing means having an output and an output that is connected to said output of said gate of said gate means, said processing means being constructed to convert the time-gated amplified signals from said output of said gate, after each electrical pulse provided to said transmitter transducer, to one voltage signal representing the cord/rubber condition of plies of the carcass of the tire; and means having an input connected to said output of said processing means and constructed to provide a visual readout based on said voltage signal, provided at said output of said processing means, that indicates the condition of plies of the carcass of the tire.

2. The system of claim 1 having a pulse-echo transducer that constitutes said transmitter transducer means and said receiver transducer means.

3. The system of claim 2 wherein the pulse-providing means comprises a main bang generator connected to the output of said clock means to be triggered by voltage signals from said clock means to send, from said output of said main bang generator, said pulse of high-frequency electrical energy to said pulse-echo transducer.

4. The system of claim 3, for the testing of a stationary tire, wherein:

said gate means has its said second input connected to said output of said bang generator; and said processing means and said means providing a visual readout comprise:

peak sensing means having an input and an output, said peak sensing means having its said input connected to said output of said gate and being constructed to provide, after each ultrasonic pulse provided to the tire by said pulse-echo transducer, a voltage signal having an amplitude corresponding to the maximum amplitude of the time-gated voltage signals provided at the output of said gate;

level sensing means having first and second inputs and an output, said level sensing means having said first input connected to said output of said peak sensing means and being constructed to provide at said output of said level sensing means a voltage signal, when the voltage signal at said first input exceeds a reference voltage provided at said second input of said level sensing means; and reject light means including a light, said reject light means having an input connected to said output of said level sensing means and being constructed to light the light while there is a voltage signal provided at the input of said reject light means from said output of said level sensing means.

5. The system of claim 4 wherein:

said level sensing means has a second output that is provided a voltage signal whenever said first output of said level sensing means is provided a voltage signal; and said means to provide a visual readout includes:

a digital voltmeter having first and second inputs, said first input of said digital voltmeter being connected to said output of said peak sensing means and said second input of said digital voltmeter being connected to said second output of said level sensing means and said digital voltmeter being constructed to provide a digital readout of the voltage provided at said first input of said digital voltmeter from said peak sensing means, except when there is a voltage signal provided at said second input of said digital voltmeter from said second output of said level sensing means.

6. The system of claim 3, for the testing of a stationary tire, wherein:

said gate means has a third input and has a second gate with an output;

said gate means has said second input connected to said output of said bang generator;

said gate means has said third input connected to said output of said pulse-echo transducer and said gate means being constructed to be responsive to a voltage signal at said first input of said gate means to open said second gate, after a predetermined delay, for a predetermined period of time to provide time-gated voltage signals at said output of said second gate, after the first voltage signal is provided by said pulse-echo transducer to said amplifier means after each pulse is provided by said pulse-providing means to said pulse-echo transducer, said delay includes the delay for the opening of said first gate and a predetermined period of time; and said processing means and said means providing a visual readout comprise:

first peak sensing means having an input and an output, said first peak sensing means having its said input connected to said output of said first gate and being constructed to provide, after each ultrasonic pulse provided to the tire by said pulse-echo transducer, a voltage signal having an amplitude corresponding to the maximum amplitude of the time-gated voltage signals provided at the output of said first gate;

second peak sensing means having an input and an output, said second peak sensing means having its said input connected to said output of said second gate and being constructed to provide, after each ultrasonic pulse provided to the tire by said pulse-echo transucer, a voltage signal having an amplitude corresponding to the maximum amplitude of the time-gated voltage signals provided at the output of said gate;

ratio sensing means having first and second inputs and an output, said ratio sensing means having its said first input connected to said output of said first peak sensing means and its said second input connected to said output of said second peak sensing means and being constructed to provide at said output of said ratio sensing means a voltage signal, whenever the ratio of the voltage signals provided to said first and second input of said ratio sensing means exceeds a predetermined value; and reject light means including a light, said reject light means having an input connected to said output of said ratio sensing means and being constructed to light the light while there is a voltage signal provided at the input of said reject light means from said output of said ratio sensing means.

7. The system of claim 6 wherein:

said ratio sensing means has a second output that is provided a voltage signal whenever said first output of said lever ratio means is provided a voltage signal; and said means to provide a visual readout includes:

a digital voltmeter having first and second inputs, said first input of said digital voltmeter being connected to said output of said first peak sensing means and said second input of said digital voltmeter being connected to said second output of said ratio sensing means and said digital voltmeter being constructed to provide a digital readout of the voltage provided at said first input of said digital voltmeter from said first peak sensing means, except when there is a voltage signal provided at said second input of said digital voltmeter from said second output of said ratio sensing means.

8. The system of claim 3, for the testing of a rotated tire, wherein:

said gate means has its second input connected to said output of said bang generator;

said processing means and said means providing a visual readout comprise:

summing means having first and second inputs and outputs, its said first input being connected to said output of said gate of said gate means, and being constructed to convert, when operative, a voltage signal at its said first input to digital signals at its said outputs;

a digital display panel having inputs connected to said outputs of said summing means and constructed to provide a visual display of digital numbers representing digital signals provided at said outputs of said summing means; and cycle control means having an output connected to said second input of said summing means and operative to provide a signal to that input of said summing means for the period of a complete revolution of the tire being inspected so that the summing means operates on all time-gated voltage signals at the output of said gate means during the complete revolution of the tire.

9. The system of claim 1 for the testing of a stationary tire, wherein:

said processing means comprises voltage integrator means having an integrator with an input and an output, said input of said integrator being connected to said output of said gate of said gate means and said output of said integrator being connected to said visual readout; and said visual readout comprises voltage indicator means having its input connected to said output of said integrator.

10. The system of claim 9 having a pulse-echo transducer that constitutes said transmitter transducer means and said receiver transducer means and wherein said gate means has its said second input connected to said output of said bang generator.

11. A pulse ultrasonic reflection system for residual tire life prediction, which comprises:

imparting pulses of ultrasonic energy into an area of a tire in a manner to provide pulses of reflected acoustic energy so that each reflected pulse includes reflected ultrasonic energy from the plies of the carcass of the tire;

converting the pulses of reflected acoustic energy to pulses of electrical signals;

amplifying the electrical signals;

processing the pulses of amplified electrical signals to provide information with respect to the amplitude of those amplified electrical signals based on the reflected acoustic energy from at least one of the plies of the carcass;

determining the difference between that information and information obtainable by the same processing of amplified signals from acoustic energy reflected from the same ply or plies of an unused, new tire that is the same type and that has a satisfactory ply construction and has a satisfactory bonding of the cords to the rubber matrix of the tire carcass; and predicting from that difference the extent of circumferential degradation and thus the life of the tire being tested by the system.

12. The system of claim 11 in which the steps of imparting pulses of ultrasonic energy and receiving pulses of reflected acoustic energy are provided by using a pulse-echo transducer and the pulses of ultrasonic energy are applied to the surface of the tread of the tire.

13. The system of claim 12 in which the system is performed a number of times only at a small portion of the periphery of the tire.

14. The system of claim 12 in which, in the event that the information obtained from the tire being tested is greater than that obtainable from a satisfactory new, unused tire, the tire is tested at least at a number of areas about the tire to determine that the information is due to circumferential degradation or to a localized defect.

* * * * *

UNITED STATES PATENT AND TRADEMARK OFFICE
CERTIFICATE OF CORRECTION

PATENT NO. : 4,089,225
DATED : May 16, 1978
INVENTOR(S) : Irvin R. Kraska et al.

It is certified that error appears in the above-identified patent and that said Letters Patent are hereby corrected as shown below:

```
Column  3, line 36, "upply" should read --supply--.
Column  7, line 37, "the reference" should read --The reference--.
Column  8, line 34, "claim 3" should read --FIG. 3--.
Column 12, line 60, "output" should read --input--.
Column 14, line 61, "value" should read --numerical value--.
Column 17, line 61, "inspection" should read --inspection
                    system--.
Column 19, line 27, "FIG. 3" should read --FIG. 5--.
Column 21, line 27, "output that" should read --input that--.
           Line 39, "condition" should read --cord/rubber
                    condition--.
Column 22, line 67, "transucer" should read --transducer--.
Column 23, line 11, "input" should read --inputs--.
           Line 23, "lever" should read --level--.
```

Signed and Sealed this

Twenty-fourth Day of October 1978

[SEAL]

Attest:

RUTH C. MASON
Attesting Officer

DONALD W. BANNER
Commissioner of Patents and Trademarks